United States Patent
Cross et al.

(10) Patent No.: US 10,556,059 B2
(45) Date of Patent: Feb. 11, 2020

(54) INFUSION PUMP DRIVE WITH COMPRESSION SPRING

(71) Applicant: Biogen MA Inc., Cambridge, MA (US)

(72) Inventors: David Cross, Letchworth (GB); Michael Paton, Royston (GB)

(73) Assignee: Biogen MA Inc., Cambridge, MA (US)

( * ) Notice: Subject to any disclaimer, the term of this patent is extended or adjusted under 35 U.S.C. 154(b) by 286 days.

(21) Appl. No.: 15/108,999

(22) PCT Filed: Dec. 22, 2014

(86) PCT No.: PCT/US2014/071838
§ 371 (c)(1),
(2) Date: Jun. 29, 2016

(87) PCT Pub. No.: WO2015/102987
PCT Pub. Date: Jul. 9, 2015

(65) Prior Publication Data
US 2016/0317738 A1   Nov. 3, 2016

Related U.S. Application Data

(60) Provisional application No. 61/962,308, filed on Dec. 31, 2013.

(51) Int. Cl.
*A61M 5/145* (2006.01)
*A61M 5/168* (2006.01)

(52) U.S. Cl.
CPC ...... *A61M 5/1454* (2013.01); *A61M 5/16881* (2013.01); *A61M 2005/14506* (2013.01)

(58) Field of Classification Search
CPC .. A61M 5/142; A61M 5/14216; A61M 5/145; A61M 5/1452; A61M 5/31515;
(Continued)

(56) References Cited

U.S. PATENT DOCUMENTS 4,064,879 A * 12/1977 Leibinsohn ........... A61M 5/486
604/121
4,457,752 A    7/1984 Vadasz
(Continued)

FOREIGN PATENT DOCUMENTS

EP   1 920 793 A1   5/2008
EP   2 042 210 A2   4/2009
(Continued)

OTHER PUBLICATIONS

International Search Report and Written Opinion for Application No. PCT/US2014/071838, dated Mar. 31, 2015

*Primary Examiner* — Nathan R Price
*Assistant Examiner* — Dung T Ulsh
(74) *Attorney, Agent, or Firm* — Wolf, Greenfield & Sacks, P.C.

(57) ABSTRACT

An infusion pump drive and its methods of use are disclosed. In one embodiment, the infusion pump drive may include a transmission component and a spring in line with the transmission component. Displacing the transmission component may compress the spring to apply a force causing fluid to dispense from an associated reservoir. Depending on the particular embodiment, the transmission component may either be displaced continuously or displaced multiple times to dispense fluid from the reservoir.

44 Claims, 5 Drawing Sheets

(58) Field of Classification Search
CPC ......... A61M 2005/14506; A61M 2005/31516; A61M 2005/31523; F04B 9/06
See application file for complete search history.

(56) References Cited

U.S. PATENT DOCUMENTS

| | | | | |
|---|---|---|---|---|
| 4,857,056 A | * | 8/1989 | Talonn | A61M 5/1454 604/135 |
| 5,318,539 A | | 6/1994 | O'Neil | |
| 6,030,363 A | | 2/2000 | Kriesel | |
| 2005/0159708 A1 | | 7/2005 | Sidler | |
| 2005/0165384 A1 | * | 7/2005 | Gravesen | A61M 5/141 604/890.1 |
| 2006/0069382 A1 | * | 3/2006 | Pedersen | A61K 9/0004 604/890.1 |
| 2010/0130932 A1 | * | 5/2010 | Yodfat | A61M 5/14248 604/151 |
| 2011/0097229 A1 | | 4/2011 | Cauley et al. | |
| 2012/0065502 A1 | * | 3/2012 | Levy | A61M 5/007 600/431 |
| 2013/0090605 A1 | | 4/2013 | O'Connor et al. | |
| 2013/0341352 A1 | * | 12/2013 | Williams | B05B 11/048 222/95 |
| 2015/0209505 A1 | * | 7/2015 | Hanson | A61M 5/1454 604/135 |
| 2016/0074588 A1 | * | 3/2016 | Butler | A61M 5/20 604/211 |

FOREIGN PATENT DOCUMENTS

| | | |
|---|---|---|
| WO | WO 91/14467 A1 | 10/1991 |
| WO | WO 2006/055834 A2 | 5/2006 |
| WO | WO 2011/046950 A1 | 4/2011 |
| WO | WO 2013/127428 A1 | 9/2013 |

\* cited by examiner

INFUSION PUMP DRIVE WITH COMPRESSION SPRING

CROSS REFERENCE OF RELATED APPLICATIONS

This Application is a national stage filing under 35 U.S.C. § 371 of International Patent Application Ser. No. PCT/US2014/071838, filed Dec. 22, 2014, which claims the benefit of priority under 35 USC § 119(e) of U.S. Provisional Application Ser. No. 61/962,308, filed Dec. 31, 2013, the disclosures of each of which are incorporated herein by reference in their entirety.

FIELD

Disclosed embodiments are related to an infusion pump drive.

BACKGROUND

Infusion pumps are typically used to deliver controlled amounts of a fluid to a patient at low flow rates and/or large volumes over an extended period of time. For example, infusion pumps may administer dosages as low as about 0.1 ml per hour. Alternatively, infusion pumps might also be used with high viscosity fluids and/or high flow rates where relatively large forces may be applied by the infusion pump over long periods of time. Typical fluids delivered include medications and/or nutrients. Infusion pumps may be used to deliver a fluid intravenously, subcutaneously, or epidurally depending on a desired application. Additionally, an infusion pump may be operated to provide continuous infusion, intermittent infusion, or patient-controlled infusion depending on the particular medical needs of a patient. Infusion pumps may be large pumps intended for use in a hospital or office setting, or they may be sized such that they may be carried by, or implanted within, a patient to permit them to go about their daily routine.

SUMMARY

In one embodiment, an infusion pump drive includes a transmission component and a spring in line with the transmission component. Displacement of the transmission component compresses the spring to apply a force to a stopper that is moveable within a reservoir, movement of the stopper in response to the applied force causing a fluid to dispense from the reservoir.

In another embodiment, a method includes displacing in an infusion pump a transmission component a first time by a first distance, wherein displacing the transmission component compresses a spring to apply a first force to a stopper, and wherein the applied first force displaces the stopper in a reservoir causing fluid to dispense from the reservoir.

In yet another embodiment, a method includes compressing a spring associated with a stopper in an infusion pump to a first length, and expanding the spring to a second length greater than the first length, wherein expanding the spring displaces the stopper in a reservoir to dispense a volume of fluid from the reservoir, and wherein the volume of dispensed fluid is less than a total volume of the reservoir.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
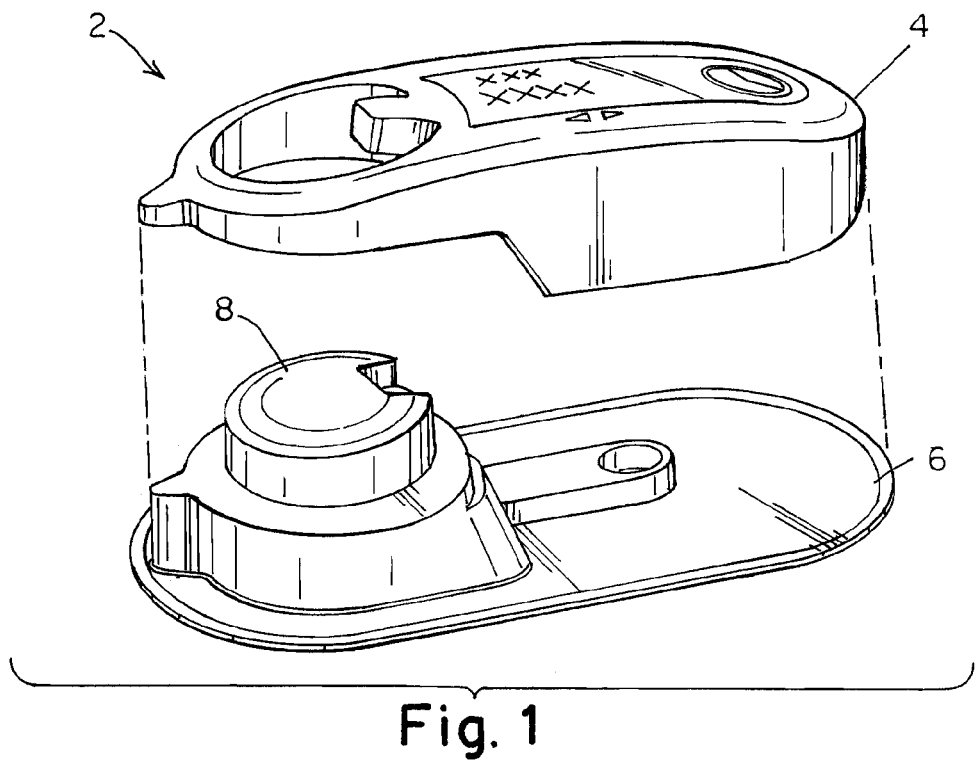
FIG. 1 is a schematic perspective view of an infusion pump including a reusable portion and a disposable portion.

The inventors have recognized the benefits associated with providing an infusion pump with a hybrid drive including a spring arranged in line with a displaceable component of a transmission. During operation, the spring may be selectively compressed by the transmission component to apply a force, such as to a stopper associated with a reservoir, or to a compressible reservoir. As described in more detail below, depending on the particular embodiment, the spring may either be compressed by a desired displacement and allowed to expand, or the spring may be continuously displaced. Additionally, this displacement may either be a linear displacement or a rotational displacement depending on the particular type of spring used as the disclosure is not so limited. However, as described in more detail below, regardless of the manner in which the spring is compressed, the force applied to the stopper by the spring may displace the stopper and dispense fluid from the reservoir.

An infusion pump including a hybrid drive as described herein may be used to dispense any appropriate fluid from within a reservoir of an infusion pump. For example, the fluid might be used to deliver nutrients as well as medications such as insulin, antibiotics, chemotherapy drugs, and pain relievers. Additionally, the hybrid drive may be used in different types of infusion pumps. For instance, in some embodiments, a hybrid drive might be used for mobile applications such as an infusion pump that is applied to a patient's skin using an adhesive or that is implanted within a patient. In other embodiments, a hybrid drive may be used in a larger infusion pump suitable for hospital and/or medical office settings. In view of the above, the hybrid drives described herein should not be limited to any particular type of infusion pump or therapeutic use as the disclosure is not so limited.

In one embodiment, a hybrid drive may include a compression spring, such as a coil spring, that is positioned in line with a displaceable piston, or other appropriate transmission component, and a stopper moveable within a reservoir. The piston may be displaced to compress the compression spring, applying a force; for example, to move an associated stopper in a reservoir or to compress a reservoir. In another embodiment, a hybrid drive may include a torsional spring, such as a helical torsion spring. In such an embodiment, the torsional spring may be in line with a rotating shaft such that it transmits a force from the shaft through the torsional spring. Alternatively, a linearly displaceable element might be positioned in line with an end of the torsional spring in order to apply the desired compression to the spring which will in turn transmit a force.

Without wishing to be bound by theory, the use of a torsional spring may help to reduce the size of the overall hybrid drive due to torsional springs generally being more compact than compression springs. Additionally, the possibility of using a more compact rotational shaft to bias the torsional spring, as compared to a longer piston or other linearly displaced element, may also help to reduce the size of the hybrid drive as well.

A hybrid drive may be driven by an associated motor, or they could also be driven using a manually actuated system as the current disclosure is not so limited. Additionally, it should be understood that any appropriate element, or combination of elements, capable of compressing a spring to apply a desired force to a stopper and dispense fluid from an associated reservoir is contemplated. For example, while the embodiments described herein do not specifically include gear trains, clutches, and various other types of couplings, the possibility of a hybrid drive including these components is also contemplated.

For the sake of clarity, the embodiments described below are primarily directed to a hybrid drive including a piston arranged in line with a compression spring. However, as noted above, the disclosure should not be limited to only embodiments including compression springs and linearly displaced pistons. Instead, it should be understood that a hybrid drive might use any appropriate spring associated with a transmission component capable of biasing the spring to apply a force to a stopper, other component associated with a reservoir, or to the reservoir itself, to dispense a fluid. Additionally, while embodiments including a hybrid drive acting on a stopper are shown for clarity, a hybrid drive might be used with other configurations of pistons, reservoirs, and stoppers as well. For example, a hybrid drive may act on a reservoir in the form of a prefilled compressible bellows type reservoir which would not require a stopper. In such an embodiment, force from a hybrid drive might be applied directly to the reservoir to dispense the fluid.

In addition to the above, while particular arrangements are described in more detail below, it should be understood that the described pistons, or other appropriate transmission components, might be monolithic, flexible, rigid, segmented, or have any other desired characteristic as the disclosure is not so limited. The piston also might be linearly displaceable and associated with a compression spring, rotationally displaceable (e.g., screw in plunger) and associated with a torsional spring, or other configurations as should be apparent to one of skill in the art as the disclosed embodiments are not limited to any particular method of displacement. Additionally, it should be understood that the while the spring might be located between the piston and the stopper, the spring might also be located elsewhere between the motor and the stopper as the disclosure is not limited as to where the spring is located. For example, the spring might be located between a pinion gear, associated with the motor, and the stopper. Therefore, depending on the embodiment, the spring may or may not be in contact with the stopper. Whether there is direct or indirect contact between the spring and the stopper, the spring is "operatively associated" with the stopper.

Having described the various general embodiments of a hybrid drive, two non-limiting modes of operation for a hybrid drive are described below.

In a first embodiment, a hybrid drive includes a spring in line with a transmission component and may be operated by continually displacing the transmission component to dispense a fluid from an infusion pump. As the transmission component is displaced, the spring is compressed and applies a force to a stopper associated with the spring to dispense fluid from a reservoir. Without wishing to be bound by theory, if the transmission component is displaced at a constant rate, the spring will reach a substantially constant compression and will apply a substantially constant force to the associated stopper. Additionally, in instances where the stopper sticks within the reservoir during actuation, for example a piston stopper combination sticking within a syringe, the transmission component may continue to be displaced which may result in increased spring compression and increased force being applied to the stopper. As the amount of compression and force continues to increase, the applied force will overcome this stiction and the spring may once again expand to the substantially constant amount of compression and the force applied to the stopper may also return to the substantially constant force noted above. Thus, operating the hybrid drive in a continuous fashion may help to provide a substantially constant force to a stopper which may result in a substantially constant flow rate from the associated reservoir. Continuously displacing the hybrid drive in this fashion may also help to mitigate force spikes associated with a rigid drive overcoming stiction friction at low displacement rates common with infusion pumps. While a constant displacement rate is described above, embodiments in which the transmission component associated with the spring is displaced at non-constant rates are also possible.

In a second embodiment, a hybrid drive including a spring in line with a transmission component may be operated such that the spring undergoes one or more displacement and expansion cycles to dispense a fluid from an infusion pump. In such an embodiment, the transmission component and the associated spring are sequentially displaced to dispense multiple doses of a fluid within an associated reservoir. During this mode of operation, the transmission component is displaced a first distance to compress the spring to a first length. Again, this length may either be a rotational or linear length as the disclosure is not limited in this fashion. The spring is then allowed to expand from the first length to a second length greater than the first length. This second length may correspond to an uncompressed length of the spring, or it may correspond to a length less than the uncompressed length of the spring. As the spring is compressed and subsequently expanded, the spring applies a force to the associated stopper to dispense fluid from the reservoir. After the spring has expanded to the desired length, the transmission component is displaced again to begin another cycle of compressing and subsequently expanding the spring to dispense additional fluid from the reservoir. The transmission component and associated spring may undergo multiple compression and expansion cycles until either a desired amount, or all, of the fluid within the reservoir has been dispensed. The timing of the transmission component displacement may be controlled in any number of ways. For example, the transmission component may be displaced after a force threshold, pressure threshold, time threshold, flow rate threshold, and/or any other appropriate threshold is sensed.

Operating a hybrid drive using multiple sequential displacement and expansion cycles may offer multiple benefits as compared to typical drives used in infusion pumps. For example, hybrid drives operated in this fashion may offer up to about 10 times greater efficiencies than comparable direct drive motors that are operated continuously. Without wishing to be bound by theory, this is due to the motors associated with the hybrid drive operating at faster motor speeds for a fraction of the time as compared to operating at slower speeds for the entire time. This may allow the use of a more efficient standard DC micro motor operating near its peak efficiency speed. In one exemplary embodiment, a DC micro motor might be actuated four separate times for a period of 16 seconds at 6000 RPM to deliver a 10 ml dose. This is in comparison to a direct drive motor operating for 3000 seconds at 100 RPM to deliver the same 10 ml dose.

In the embodiments described above, a spring used in a hybrid drive was assumed to be uncompressed prior to the displacement of an associated transmission component. However, the disclosure is not limited to embodiments in which the spring is initially uncompressed. Therefore, in some embodiments, the spring may be compressed prior to displacement of the transmission component. Such an embodiment may allow the spring to apply a force and dispense fluid from an associated reservoir at the beginning of actuation without the need to displace the piston first. Such an embodiment may offer multiple benefits. For example, the fluid may be dispensed more quickly during initial actuation since it does not require the piston to be displaced to begin dispensing fluid. Additionally, since the spring is initially compressed, the overall hybrid drive may have a reduced length as compared to similar direct drives. Depending on the particular mode of operation, the piston may either be displaced at the same time as the spring is released such that it operates in a continuous displacement mode, or the spring may be allowed to expand prior to displacing the spring such that it operates using multiple displacement and expansion cycles as described above.

In view of the various modes of operation noted above for a hybrid drive, a transmission component may be displaced using a single stroke, or it may undergo multiple displacements to travel the full stroke length of the hybrid drive. Therefore, depending on the embodiment, the hybrid drive may be operated such that it undergoes a single displacement, two displacements, three displacements, four displacements, five displacements, or any other appropriate number of displacements to go through a full stroke length of the hybrid drive. In view of the above, the hybrid drive may undergo one or more displacements that correspond to about 100%, 50%, 33.3%, 25%, 20%, or any other appropriate percentage of a full stroke length. In instances where the hybrid drive undergoes multiple displacements, these displacements may either be substantially equal to one another to dispense substantially equal amounts of fluid, or they may be varied to deliver different amounts of fluid as the disclosure is not so limited. For example, the hybrid drive might undergo a first displacement corresponding to 50% of a full stroke length and a second displacement corresponding to 25% of a full stroke length.

It should be understood that the components of a hybrid drive may be provided within an infusion pump in any number of different ways. For example, in one embodiment, the infusion pump may be a single device including the entire hybrid drive. Alternatively, in another embodiment, the infusion pump may include a reusable portion and a disposable portion. In such an embodiment, the various portions of the hybrid drive can either be included in the reusable portion or the disposable portion as the disclosure is not so limited. For example, in one possible embodiment, a motor as well as an associated piston and spring may be located within the reusable portion of an infusion pump and a stopper adapted and arranged to interact with the spring may be located within the disposable portion of the infusion pump. Various other combinations of components on the reusable portion versus the disposable portion are also possible. Additionally, while a device with a reusable portion and a disposable portion has been depicted, it should be understood that the entire device could also be disposable or reusable as the disclosure is not so limited.

In addition to providing a drive to control the dispensing of fluid from an associated reservoir, in some embodiments, an infusion pump may also include appropriate mechanisms to further control the flow of a fluid being dispensed from the infusion pump. For instance, a component to control the flow restriction through an outlet of the reservoir may be used to control the flow. One possible component to control the flow restriction includes, but is not limited to, a valve such as a pinch valve, a duck bill valve, a check valve, or any other appropriate valve. Without wishing to be bound by theory, controlling the flow restriction relative to a pressure applied to the reservoir may be used to provide a more stable, i.e. constant, flow rate from the reservoir. For example, the flow restriction of an outlet of the reservoir may be increased for higher applied pressures and decreased for lower applied pressures to provide a more constant flow rate over a larger range of pressures. While the flow restriction from the reservoir may be controlled to provide a substantially constant flow rate, in other embodiments, the flow restriction might also be controlled to provide variable flow rates as the current disclosure is not so limited. Alternatively, instead of controlling the flow restriction, a valve associated with an outlet of the reservoir might be opened and closed to selectively open or close an outlet of the reservoir. For instance, the valve might be opened and closed using pulse modulation based on the applied pressure, force, or other appropriate variable to provide a substantially constant, or other desired, flow of fluid from the reservoir for a range of applied forces and pressures.

Turning now to the figures, several non-limiting embodiments are described in more detail.

Figure 2:
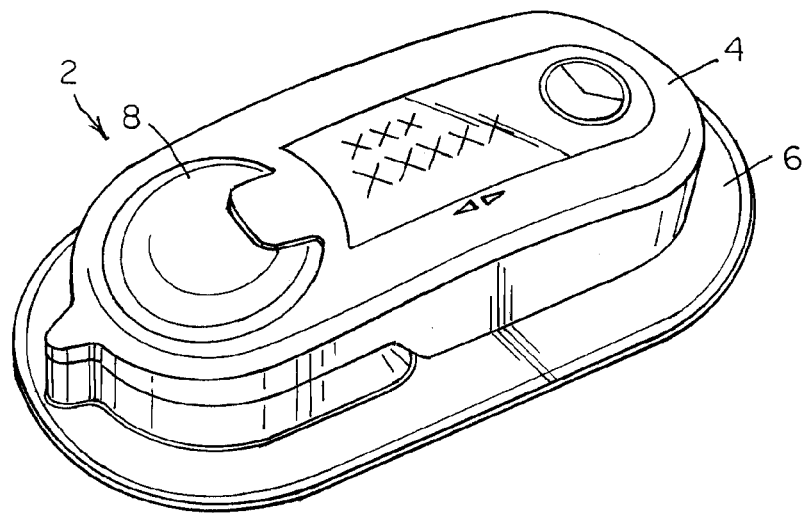
FIG. 2 is a schematic perspective view of the infusion pump of FIG. 1 with the reusable portion and the disposable portion assembled.
Figure 3:
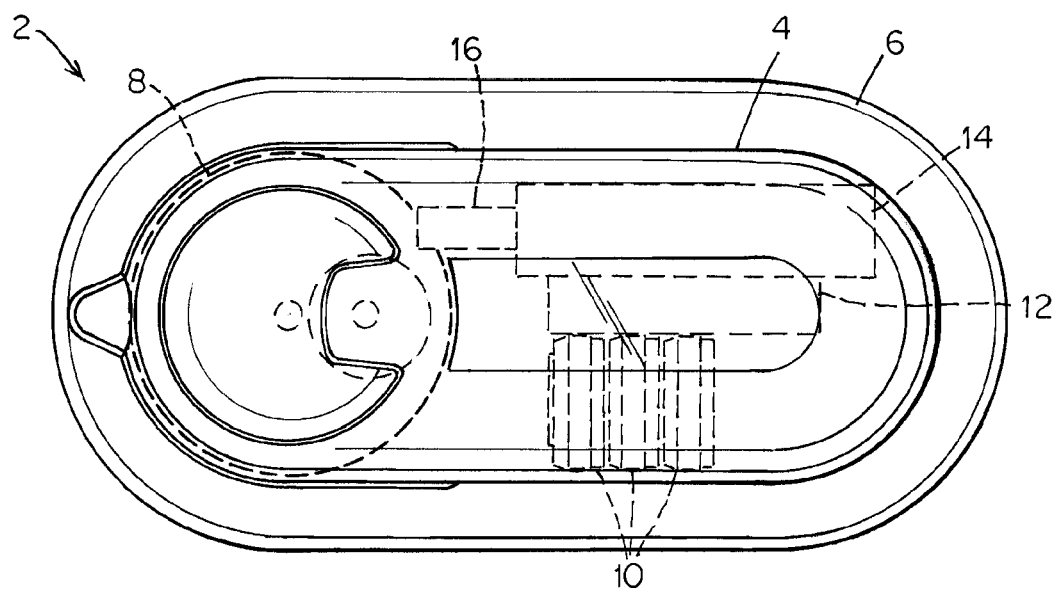
FIG. 3 is a schematic top view illustrating the relative positioning of components within an infusion pump interior.

FIGS. 1 and 2 depict an infusion pump 2. The infusion pump 2 may include a reusable portion 4 and a disposable portion 6. As shown in the figures, the disposable portion 6 may include a reservoir 8. As illustrated in FIG. 3, the infusion pump 2 may also include batteries 10, a controller 12, a motor 14, and a transmission component 16. In this embodiment, the transmission component may include a worm gear that either directly, or indirectly, engages a component on the disposable portion 6 to dispense fluid from the reservoir. As discussed above, a hybrid drive may be included either completely on the reusable portion 4, or alternatively, a portion of the hybrid drive may be included on the disposable portion 6 as the current disclosure is not so limited. Consequently, a spring, such as a torsion spring not depicted, might be located upstream of the transmission component 16 within the reusable portion 4, or downstream of the transmission component 16 within the disposable portion 6, as the disclosure is not so limited. The controller 12 may be located on the reusable portion 4 or the disposable portion 6 and may control operation of the motor 14 according to the various embodiments described herein.

Figure 4:
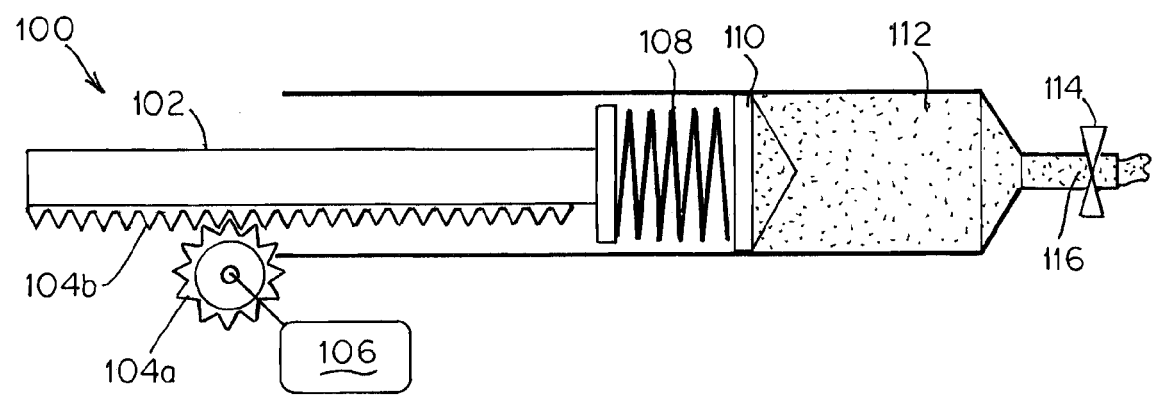
FIG. 4 is a schematic representation of a hybrid drive.

FIG. 4 depicts one exemplary embodiment of a hybrid drive 100. The hybrid drive 100 may include a transmission with components such as rack and pinion gears 104a and 104b as well as a piston 102 associated with the rack and pinion gears. As depicted in the figures, the hybrid drive 100 may also include a motor 106 drivingly connected to the pinion gear 104a such that when the motor 106 drives the pinion gear 104a the rack 104b displaces the piston 102. The hybrid drive 100 may also include a spring 108 that is arranged in line with the piston 102 of the transmission. The spring 108 may be positioned such that it is disposed between the piston 102 and a stopper 110. When the piston 102 is displaced, the spring 108 is compressed and applies a force to the stopper 110. The applied force displaces the stopper 110 in a fluid reservoir 112, causing fluid to dispense from the reservoir. Depending on the embodiment, a difference between the fully compressed and free length of the spring 108, linear or rotational, may be less than, equal to, or greater than a length of travel of the piston 102, or other appropriate transmission component.

While fluid flow from the reservoir 112 may be controlled using the force applied to the stopper, directly or indirectly, by the spring, the flow rate may also be controlled using a controllable valve 114, such as a pinch valve, duck bill valve, check valve, or other appropriate valve, to alter the flow resistance from an outlet 116 of the reservoir. In some embodiments, an outlet 116 of the reservoir 112 may pass through the valve 114 without being pierced by the valve. This may permit the valve and other portions of the hybrid drive to be reusable with a disposable reservoir and outlet. The valve may also be associated with a locking button to selectively permit, or prevent, dispensing of fluid. Other appropriate locking mechanisms are also possible While a piston that is linearly in line with a spring has been depicted in the figures, other embodiments of a transmission component that is in line with an associated spring are also possible. For example, a rotatable shaft arranged perpendicular to a torsional spring and associated stopper might also be considered to be in line with the spring. Additionally, embodiments in which the spring is axially offset from an associated piston and stopper, but still transmits the applied force from the piston to the stopper might also still be considered to be in line with the piston and the stopper.

Figure 5:
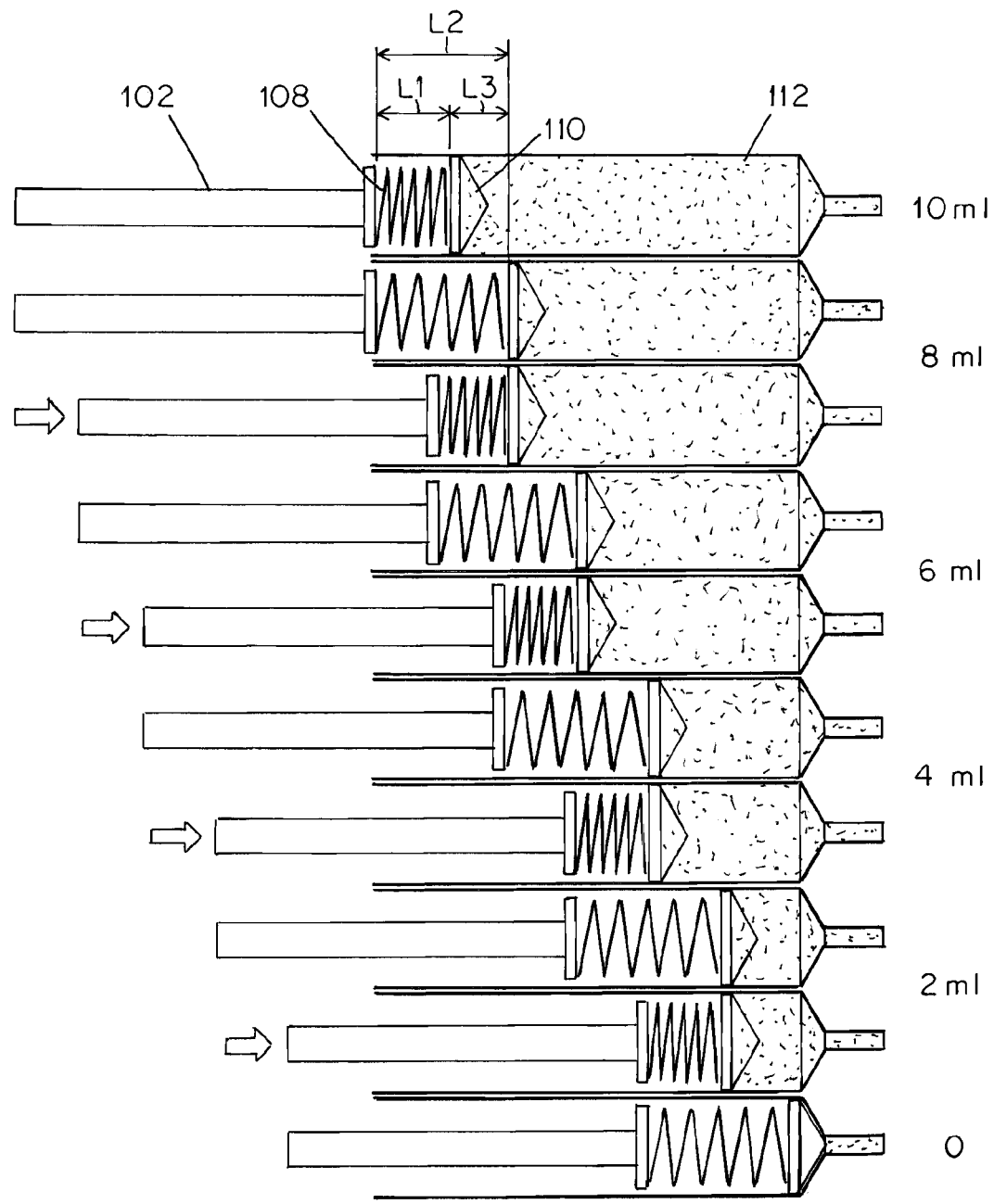
FIG. 5 is a schematic representation of the use of the hybrid drive of FIG. 4.

FIG. 5 depicts one possible method of operating the hybrid drive depicted in FIG. 4. As illustrated in the figure, a piston 102 is in a fully extended initial position and an associated spring 108 is restrained at a compressed first length L1 using an appropriate restraining mechanism, not depicted. The compressed spring 108 is associated with a stopper 110 and a reservoir 112 is provided as described above. In the depicted embodiment, the reservoir 112 has an initial capacity of 10 ml. After the compressed spring 108 is released, the spring expands from the first length L1 to a second length L2 greater than the first. As the spring 108 expands, it applies a force to the stopper 110 which displaces the stopper in the reservoir 112 causing fluid to dispense therefrom. In the embodiment depicted in the figures, the difference between the first and second lengths is selected to dispense 2 ml from the reservoir though any length corresponding to a desired volume displacement could be selected.

After the spring 108 has expanded to the second length L2, the piston 102 is displaced by a distance L3 equal to a difference between the first length L1 and second length L2. This displacement of the piston compresses the spring 108 to the first length L1 again. The spring is again permitted to expand from the first length L1 to the second length L2 to dispense another 2 ml from the reservoir 112. The displacement of the piston 102 may be actuated when a sensed force, pressure, flow rate, time period, or other appropriate metric passes an established activation threshold.

This process of sequentially displacing the piston to compress and expand the spring to dispense fluid from the reservoir may be continued until either a desired amount of fluid has been dispensed from the reservoir, or the reservoir has been emptied as depicted in the figure. In this particular embodiment, five separate 2 ml doses are dispensed from the reservoir 112 using the depicted hybrid drive. While equivalent displacements of the piston and compressions of the spring are shown in the figure, different amounts of spring compression and piston displacement during the individual actuations are possible. Additionally, while an initial compression of the spring 108 has been depicted as being equal to the distance L3, any appropriate amount of pre-compression greater than or equal to that distance is contemplated. Additionally, embodiments in which no pre-compression of the spring is used are also contemplated.

While FIG. 5 depicts an operation mode using multiple actuations to dispense multiple discrete doses of a fluid contained within the reservoir, as noted above, a hybrid drive may also be actuated using a single displacement of a piston, or other transmission. Therefore, it should be understood that uses of a hybrid drive should not be limited to only the modes of operation described herein.

In addition to the above, while a single hybrid drive associated with a single reservoir or syringe has been depicted in the figures, embodiments in which one or more hybrid drives are associated with a single syringe or, instead, with two or more adjacent syringes or reservoirs are also contemplated. For example, one or more hybrid drives might be used to sequentially deliver fluid from two or more parallel syringes or reservoirs or to deliver fluid from both syringes or reservoirs at the same time. A single hybrid drive may include a motor associated with one or more springs used to drive the transmission components of the two or more adjacent syringes or reservoirs. Therefore, it should be understood that the disclosed hybrid drives are not limited to use with any particular number of syringes or reservoirs.

Example: Device Comparison

Figure 6:
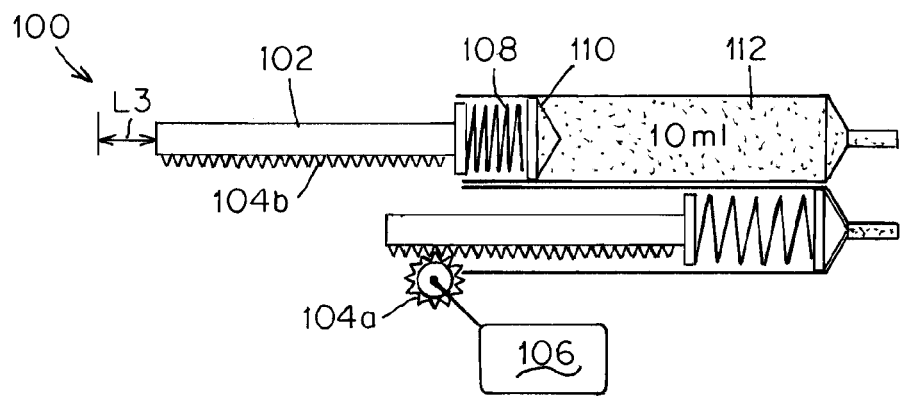
FIG. 6 is a schematic representation of a hybrid drive.
Figure 7:
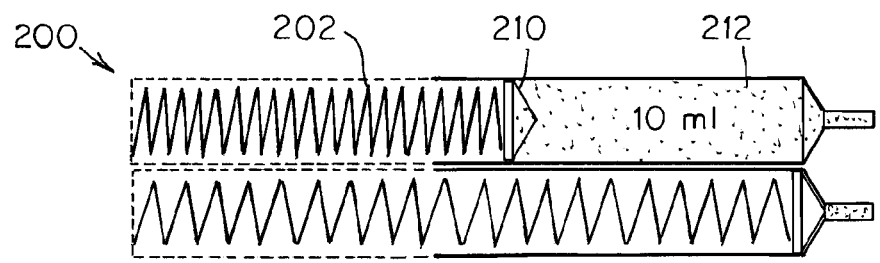
FIG. 7 is a schematic representation of a simple spring drive.
Figure 8:
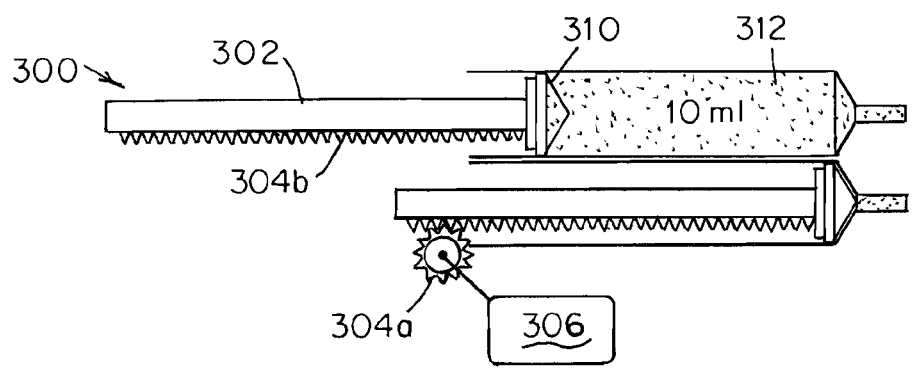
FIG. 8 is a schematic representation of a direct drive.

FIGS. 6-8 provide a comparison of a hybrid drive 100 with a simple spring drive 200 and a direct drive 300.

Similar to the embodiments described above, the hybrid drive 100 may include a piston 102 that is driven by a rack and pinion gear combination 104a and 104b coupled to a motor 106. As the piston 102 is displaced, a spring 108 in line with the piston drives an associated stopper 110 to dispense fluid from an associated reservoir 112. The depicted simple spring drive 200 includes a spring 202 that is initially compressed to displace the stopper 210 and dispense fluid from the reservoir 212 as it expands from its initially compressed length to the full stroke length of the spring drive. The direct drive 300 includes a piston 302 which is driven by an associated rack and pinion gear combination 304a and 304b drivenly connected to a motor 306. However, unlike a hybrid drive, the direct drive 300 simply displaces the piston 302 to directly drive the stopper 310 and dispense fluid from the reservoir 312. As also illustrated in the figures, the piston 102 of the hybrid drive may be shorter than the piston 302 of the direct drive since the spring 108 is initially compressed by a length L3 which may correspond to a difference between the compressed and uncompressed lengths of the spring 108.

Example: Performance Comparison

Figure 9:
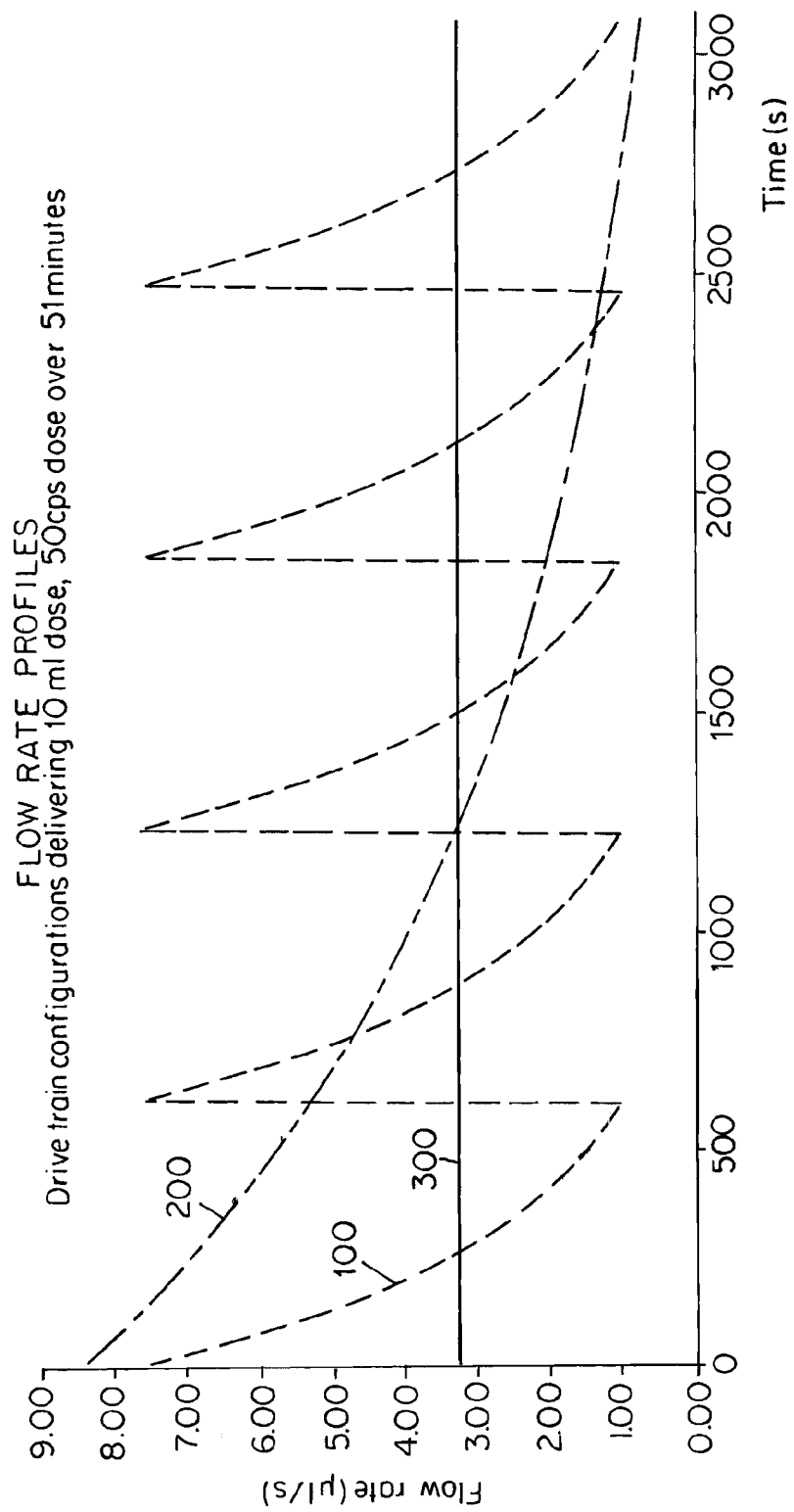
FIG. 9 is a graph of the flow rate versus time for a simple spring drive, a direct drive, and a hybrid drive.

FIG. 9 presents simulated flow rates versus time for delivering a 10 ml dose using a hybrid drive 100, a simple spring drive 200, and a direct drive 300 similar to those depicted in FIGS. 6-8. The simulated flow rates were calculated using the force and extension applied by each drive over the course of fluid delivery.

As illustrated in the graph, the direct drive 300 shows a constant flow rate of about 3.3 μl/s for the entire 3000 second time period. In contrast, the simple spring drive 200 shows an initial flow rate of about 8.5 μl/s which tapers to about 0.8 μl/s over the 3000 second time period. These illustrated overall behaviors are typical for these types of drives.

In contrast to the more typical drives, the hybrid drive 100 shows five discrete portions corresponding to compression and expansion of the spring to dispense five separate doses of fluid from the device. The first discrete portion corresponds to the expansion of the spring from an initially compressed state and the subsequent portions correspond to the piston being displaced to compress the spring and the spring subsequently expanding to dispense fluid from the device. Within each of these portions of the hybrid drive, the flow rate decreases from an initial flow rate of about 7.6 μl/s to about 1 μl/s after about 600 seconds. This process is continued until the full 10 ml does is dispensed.

In view of the above, the hybrid drive 100 provides fluid from a reservoir in a more evenly distributed fashion as compared to a simple spring drive. However, the hybrid drive 100 also provides fluid from the reservoir in a less distributed fashion when compared to a direct drive. It should be noted though, that while the hybrid drive does not offer the same distributed dosage delivery of a direct drive device, the hybrid drive does offer an additional benefit of increased efficiency. It should be understood that the fluid delivery rate and delivery profile provided by a hybrid drive and a method of dispensing a fluid disclosed herein may be modified by varying one or more of motor torque, motor speed, spring compression constant, the amount of spring compression, fluid viscosity, and other processing parameters. Additionally, a valve, such as a pinch valve, might be associated with the reservoir in order to modulate the dosage delivery. For example, the valve might undergo pulse modulation to open and close the reservoir to provide a substantially constant dosage delivery over time while also offering the benefit of increased efficiency associated with the hybrid drive noted above.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An infusion pump drive comprising:
   a transmission;
   a spring in line with the transmission, wherein the spring is positioned between the transmission and a portion of a reservoir associated with the spring; and
   a motor operatively coupled to the transmission;
   wherein the transmission is displaceable to compress the spring causing a force to be applied by the compressed spring, the applied force sufficient to dispense a fluid from the reservoir associated with the spring.

2. The infusion pump drive of claim 1, wherein the transmission includes a piston.

3. The infusion pump drive of claim 1, wherein the transmission includes a rotating shaft.

4. The infusion pump drive of claim 1, wherein the spring is a torsion spring.

5. The infusion pump drive of claim 1, wherein the spring is a compression spring.

6. The infusion pump drive of claim 1, wherein the spring is compressed prior to an initial displacement of the transmission.

7. The infusion pump drive of claim 1, wherein the infusion pump drive is incorporated into an infusion pump.

8. The infusion pump drive of claim 7, wherein the infusion pump comprises a reusable portion and a disposable portion.

9. The infusion pump drive of claim 8, wherein the infusion pump drive is located within the reusable portion of the infusion pump.

10. The infusion pump drive of claim 8, wherein at least one of the spring and a stopper are located within the disposable portion.

11. The infusion pump drive of claim 1, further including a stopper associated with the reservoir, wherein the stopper is displaceable by the applied force of the spring to dispense the fluid from the reservoir.

12. The infusion pump drive of claim 1, further including the reservoir.

13. The infusion pump drive of claim 12, wherein the reservoir is compressible and the applied force of the spring is sufficient to compress the reservoir and dispense the fluid from the reservoir.

14. The infusion pump drive of claim 12, further comprising a valve to selectively open and close an outlet of the reservoir.

15. The infusion pump drive of claim 14, wherein the valve does not pierce the outlet.

16. The infusion pump drive of claim 1, further comprising a controller operatively coupled to the motor, wherein the controller is configured and arranged to operate the motor to displace the transmission a first time by a first distance to compress the spring to dispense the fluid from the reservoir.

17. The infusion pump drive of claim 16, wherein the first distance is equal to a full stroke of the transmission.

18. The infusion pump drive of claim 16, wherein the first distance is less than a full stroke of the transmission.

19. The infusion pump drive of claim 16, wherein the spring expands to dispense the fluid from the reservoir.

20. The infusion pump drive of claim 18, wherein the controller is configured and arranged to operate the motor to displace the transmission a second time by a second distance to compress the spring and dispense the fluid from the reservoir.

21. The infusion pump drive of claim 20, wherein the first distance and the second distance are equal.

22. The infusion pump drive of claim 14, wherein the valve is actuable to control flow from the outlet of the reservoir.

23. The infusion pump drive of claim 22, wherein the valve is actuated using pulse modulation.

24. An infusion pump drive comprising:
a transmission; and
a spring in line with the transmission, wherein the spring is positioned between the transmission and a portion of a reservoir associated with the spring;
wherein the transmission is displaceable to compress the spring causing a force to be applied by the compressed spring, the applied force sufficient to dispense a fluid from the reservoir associated with the spring, and wherein the spring has a compressed state and an uncompressed state, wherein a length difference between the compressed state and the uncompressed state is less than a full stroke length of the transmission.

25. The infusion pump drive of claim 24, further comprising a motor operatively coupled to the transmission and a controller operatively coupled to the motor, wherein the controller is configured and arranged to operate the motor to drive the transmission to alternatingly compress and expand the spring to dispense the fluid from the reservoir.

26. The infusion pump drive of claim 25, wherein expanding the spring from the compressed state to the uncompressed state dispenses a volume of the fluid from the reservoir that is less than a total volume of the reservoir.

27. An infusion pump drive comprising:
a transmission;
a spring in line with the transmission, wherein the spring has a compressed state and an uncompressed state, wherein a length difference between the compressed state and the uncompressed state is less than a full stroke length of the transmission;
a motor operatively coupled to the transmission;
a controller operatively coupled to the motor, wherein the controller is configured and arranged to operate the motor to drive the transmission to cyclically compress and expand the spring to dispense a fluid from a reservoir associated with the spring.

28. The infusion pump drive of claim 27, further comprising a stopper associated with the reservoir, wherein the spring is disposed between the transmission and the stopper.

29. The infusion pump drive of claim 27, wherein the transmission includes a piston.

30. The infusion pump drive of claim 27, wherein the transmission includes a rotating shaft.

31. The infusion pump drive of claim 27, wherein the spring is a torsion spring.

32. The infusion pump drive of claim 27, wherein the spring is a compression spring.

33. The infusion pump drive of claim 27, wherein the spring is compressed prior to an initial displacement of the transmission.

34. The infusion pump drive of claim 27, further including the reservoir.

35. The infusion pump drive of claim 34, wherein the reservoir is compressible and the applied force of the spring is sufficient to compress the reservoir and dispense the fluid from the reservoir.

36. The infusion pump drive of claim 27, further comprising a valve to selectively open and close an outlet of the reservoir.

37. The infusion pump drive of claim 36, wherein the valve does not pierce the outlet.

38. The infusion pump drive of claim 36, wherein the valve is actuatable to control flow from the outlet of the reservoir.

39. The infusion pump drive of claim 36, wherein the valve is actuated using pulse modulation.

40. The infusion pump drive of claim 1, wherein the transmission is displaceable in a distal direction to compress the spring in the distal direction causing a force to be applied to the reservoir by the compressed spring.

41. An infusion pump drive comprising:
a transmission including a rotating shaft; and
a spring in line with the transmission, wherein the spring is positioned between the transmission and a portion of a reservoir associated with the spring;
wherein the transmission is displaceable to compress the spring causing a force to be applied by the compressed spring, the applied force sufficient to dispense a fluid from the reservoir associated with the spring.

42. The infusion pump drive of claim 41, wherein the transmission includes a piston.

43. The infusion pump drive of claim 41, wherein the spring is one selected from the group of a torsion spring and a compression spring.

44. The infusion pump drive of claim 41, wherein the reservoir is compressible and the applied force of the spring is sufficient to compress the reservoir and dispense the fluid from the reservoir.

* * * * *